US010500437B1

(12) United States Patent
Eilers et al.

(10) Patent No.: US 10,500,437 B1
(45) Date of Patent: Dec. 10, 2019

(54) ELLIPTICAL EXERCISE DEVICE

(71) Applicant: Dynamis Design LLC, Denver, CO (US)

(72) Inventors: Derek Eilers, Denver, CO (US); Jonathan Charles Fearnow, Louisville, CO (US)

(73) Assignee: Dynamis Design LLC, Denver, CO (US)

( * ) Notice: Subject to any disclaimer, the term of this patent is extended or adjusted under 35 U.S.C. 154(b) by 115 days.

(21) Appl. No.: 15/784,249

(22) Filed: Oct. 16, 2017

Related U.S. Application Data

(60) Provisional application No. 62/409,182, filed on Oct. 17, 2016.

(51) Int. Cl.
*A63B 22/06* (2006.01)
*A63B 21/00* (2006.01)
(Continued)

(52) U.S. Cl.
CPC ........ *A63B 22/0664* (2013.01); *A61B 5/0066* (2013.01); *A61B 5/055* (2013.01);
(Continued)

(58) Field of Classification Search
CPC .............. A63B 21/154; A63B 21/4049; A63B 21/4034; A63B 21/225; A63B 21/0051;
(Continued)

(56) References Cited

U.S. PATENT DOCUMENTS 4,441,502 A 4/1984 Chance
5,183,453 A 2/1993 Yamashiro
(Continued)

FOREIGN PATENT DOCUMENTS

EP 1714615 A1 10/2006
EP 1887935 B1 4/2013
WO 2004078019 A2 9/2004

OTHER PUBLICATIONS

Gusso et al. Design and testing of an MRI-compatible cycle ergometer for non-invasive cardiac assessments during exercise. BioMedical Engineering OnLine [online] 2012 [retrieved on Mar. 26, 2019]. Retrieved from the Internet: <URL http://www.biomedical-engineering-online.com/content/11/1/13> (Year: 2012).*
(Continued)

*Primary Examiner* — Andrew S Lo
*Assistant Examiner* — Zachary T Moore
(74) *Attorney, Agent, or Firm* — The Law Office of Patrick F. O'Reilly, III, LLC (57) ABSTRACT

An elliptical exercise device includes a pedal assembly, the pedal assembly including at least one pedal member configured to receive a force exerted thereon by a user, the at least one pedal member configured to rotate in an elliptical pedal path when the force is exerted thereon; a drivetrain assembly operatively coupled to the pedal assembly; and a resistance assembly operatively coupled to the drivetrain assembly, the drivetrain assembly configured to transfer the motive power generated by the user from the pedal assembly to the resistance assembly, and the resistance assembly configured to provide a resistance force to oppose a rotational movement of one or more components of the resistance assembly. In some embodiments, the elliptical exercise device is configured to accommodate a user in a generally supine position, and the device is configured to be utilized with a medical imaging device.

11 Claims, 12 Drawing Sheets

(51) Int. Cl.
*A63B 21/22* (2006.01)
*A61B 5/055* (2006.01)
*A63B 21/005* (2006.01)
*A61B 5/00* (2006.01)
*A61B 8/00* (2006.01)

(52) U.S. Cl.
CPC ............ *A61B 8/44* (2013.01); *A63B 21/0051* (2013.01); *A63B 21/154* (2013.01); *A63B 21/225* (2013.01); *A63B 21/4034* (2015.10); *A63B 21/4049* (2015.10); *A63B 2208/0252* (2013.01)

(58) Field of Classification Search
CPC ........ A63B 2069/161; A63B 2069/164; A63B 2069/166; A63B 2022/0641; A63B 22/0664; A63B 23/0423; A63B 37/008; A63B 2208/0252; A61B 5/055; A61B 5/0066; A61B 8/44; A63H 17/16
See application file for complete search history.

(56) References Cited

U.S. PATENT DOCUMENTS

| | | | |
|---|---|---|---|
| 5,261,294 A | | 11/1993 | Ticer et al. |
| 5,794,621 A | | 8/1998 | Hogan et al. |
| 5,836,855 A | * | 11/1998 | Eschenbach ......... A63B 22/001 482/57 |
| 5,904,638 A | * | 5/1999 | Habing ............. A63B 22/0605 482/57 |
| 6,934,574 B1 | | 8/2005 | Damadian et al. |
| 7,651,442 B2 | | 1/2010 | Carlson |
| 8,267,842 B2 | | 9/2012 | Schocke et al. |
| 8,500,606 B2 | | 8/2013 | Nishimura |
| 9,260,156 B2 | | 2/2016 | Brewer et al. |
| 9,713,739 B2 | * | 7/2017 | Dalmia ................ A63B 21/225 |
| 2004/0259692 A1 | * | 12/2004 | Martin ............... A63B 22/0007 482/52 |
| 2009/0259121 A1 | | 10/2009 | Simonetti et al. |
| 2013/0231551 A1 | | 9/2013 | Simonetti et al. |
| 2015/0141200 A1 | * | 5/2015 | Murray ................ A63B 21/154 482/5 |

OTHER PUBLICATIONS

(Gusso) with supplementary material 3D PDF model of the ergometer [online] BioMedical Engineering OnLine [online] 2012 [retrieved on Mar. 26, 2019]. Retrieved from the Internet: <URL: <https://static-content.springer.com/esm/art%3A10.1186%2F1475-925X-11-13/MediaObjects/12938_2011_540_MOESM1_ESM.PDF> (Year: 2012).*

Bjorn Quistorff et al., "A simple calf muscle ergometer for use in a standard whole-body MR scanner," Magnetic Resonance in Medicine, Mar; 13(3): pp. 444-449, first published on Mar. 1990.

David C. Isbell et al., "Calf Muscle Perfusion at Peak Exercise in Peripheral Arterial Disease: Measurement by First-Pass Contrast-Enhanced Magnetic Resonance Imaging," Journal of Magnetic Resonance Imaging, May; 25(5): pp. 1013-1020, first published on Apr. 4, 2007.

Lode Product Brochure, "MRI Ergometer Up/Down," pp. 1-6, available at least as early as Mar. 2017.

* cited by examiner

DETAIL A
SCALE 2:1

ELLIPTICAL EXERCISE DEVICE

CROSS-REFERENCE TO RELATED APPLICATIONS

This patent application claims priority to, and incorporates by reference in its entirety, U.S. Provisional Patent Application No. 62/409,182, entitled "Elliptical Exercise Device", filed on Oct. 17, 2016.

BACKGROUND OF THE INVENTION

1. Field of the Invention

The invention generally relates to an elliptical exercise device. More particularly, the invention relates to an elliptical exercise device that can be used in conjunction with a medical imaging device (e.g., a magnetic resonance imaging (MRI) scanner) to perform patient studies under cardiac stress.

2. Background

Currently, most magnetic resonance imaging (MRI) scans are performed on patients in a state of rest which can be limiting in assessing disease since most of us do not live in a state of rest. The potential of images taken when the patient is in a stressed-state (elevated heart rate) would produce a complete new set of data for clinicians and researchers to understand the functions of the body (and diseases). This stressed state data would represent the function of the body simulating the stress of everyday activities including periods of exercise.

Exercise presents a physiological perturbation to the whole body that can be used for the evaluation of functional reserve in target tissues of interest. In systemic and pulmonary vascular disease, subclinical cardiac abnormalities are not detectable easily with standard echocardiography at rest, which is the only modality with which many institutions currently perform in coordination with exercise studies. The magnetic resonance modality is ideal for evaluation of cardiac function (imaging) and for metabolic changes (spectroscopy, MRS). Use of sensitive MRI measurements with exercise would allow researchers to investigate subtle abnormalities in left heart function under stress in diseases with systemic vascular involvement such as diabetes, and in right heart function under stress in pulmonary vascular disease.

Therefore, what is needed is an elliptical exercise device that is capable of being used by a person (e.g., a patient) disposed in a supine position. Moreover, an elliptical exercise device is needed that is compatible with medical imaging devices, such as an MRI scanner, so that a patient may use the exercise device just prior to the image of the patient's body being captured by the imaging device. Furthermore, there is a need for an elliptical exercise device that minimizes the patient knee height during exercising so that the exercise device is compatible with the knee clearance requirements of the medical imaging device.

BRIEF SUMMARY OF EMBODIMENTS OF THE INVENTION

Accordingly, the present invention is directed to an elliptical exercise device that substantially obviates one or more problems resulting from the limitations and deficiencies of the related art.

In accordance with one or more embodiments of the present invention, there is provided an elliptical exercise device configured to accommodate a user in a generally supine position. The elliptical exercise device includes a pedal assembly, the pedal assembly including at least one pedal member configured to receive a force exerted thereon by the user disposed in the generally supine position, the at least one pedal member configured to rotate in an elliptical pedal path when the force is exerted thereon; a drivetrain assembly operatively coupled to the pedal assembly; and a resistance assembly operatively coupled to the drivetrain assembly, the drivetrain assembly configured to transfer the motive power generated by the user from the pedal assembly to the resistance assembly, and the resistance assembly configured to provide a resistance force to oppose a rotational movement of one or more components of the resistance assembly.

In a further embodiment of the present invention, the elliptical exercise device further comprises a linear sliding assembly operatively coupled to the pedal assembly, the linear sliding assembly comprising a slider linkage member, a slider carriage member, a slide rail, and a crank arm, the slider linkage member operatively coupling the pedal assembly to the slider carriage member, the slider carriage member configured to slidingly engage the slide rail so as to create the elliptical pedal path, and the crank arm configured to transmit the motive power to the drivetrain assembly.

In yet a further embodiment, the pedal assembly further comprises a pedal connector rod coupled to the at least one pedal member, the pedal connector rod coupling the at least one pedal member to the slider linkage member.

In still a further embodiment, the crank arm of the linear sliding assembly is configured to rotate at a first rotational velocity and the one or more components of the resistance assembly are configured to rotate at a second rotational velocity, the second rotational velocity being greater than the first rotational velocity; and the drivetrain assembly comprises at least one drive subassembly, the at least one drive subassembly configured to produce the increase from the first rotational velocity to the second rotational velocity.

In yet a further embodiment, the at least one drive subassembly comprises one of: (i) a plurality of pulleys or a plurality of sprockets operatively coupled to one another by means of a tangential coupling element, or (ii) a plurality of gears.

In still a further embodiment, the tangential coupling element is selected from the group consisting of a belt and a chain.

In yet a further embodiment, the at least one drive subassembly comprises a plurality of drive subassemblies, a first of the plurality of drive subassemblies comprising a first plurality of pulleys or a first plurality of sprockets operatively coupled to one another by means of a first tangential coupling element, and a second of the plurality of drive subassemblies comprising a second plurality of pulleys or a second plurality of sprockets operatively coupled to one another by means of a second tangential coupling element.

In still a further embodiment, the resistance assembly comprises a flywheel rotationally coupled to the drivetrain assembly and a braking subassembly configured to inhibit a rotational movement of the flywheel.

In yet a further embodiment, the braking subassembly of the resistance assembly comprises a plurality of magnets, the plurality of magnets configured to generate an eddy current so as to inhibit the rotational movement of the flywheel.

In accordance with one or more other embodiments of the present invention, there is provided an elliptical exercise device configured to be utilized with a medical imaging device. The elliptical exercise device includes a pedal assembly, the pedal assembly including at least one pedal member configured to receive a force exerted thereon by the user, the at least one pedal member configured to rotate in an elliptical pedal path when the force is exerted thereon; a drivetrain assembly operatively coupled to the pedal assembly; a resistance assembly operatively coupled to the drivetrain assembly, the drivetrain assembly configured to transfer the motive power generated by the user from the pedal assembly to the resistance assembly, and the resistance assembly configured to provide a resistance force to oppose a rotational movement of one or more components of the resistance assembly; and a base assembly coupled to the pedal assembly, the base assembly configured to be attached to the medical imaging device so as to secure the elliptical exercise device to a portion of the medical imaging device.

In a further embodiment of the present invention, the elliptical exercise device further comprises a linear sliding assembly operatively coupled to the pedal assembly, the linear sliding assembly comprising a slider linkage member, a slider carriage member, a slide rail, and a crank arm, the slider linkage member operatively coupling the pedal assembly to the slider carriage member, the slider carriage member configured to slidingly engage the slide rail so as to create the elliptical pedal path, and the crank arm configured to transmit the motive power to the drivetrain assembly.

In yet a further embodiment, the crank arm of the linear sliding assembly is configured to rotate at a first rotational velocity and the one or more components of the resistance assembly are configured to rotate at a second rotational velocity, the second rotational velocity being greater than the first rotational velocity; and the drivetrain assembly comprises at least one drive subassembly, the at least one drive subassembly configured to produce the increase from the first rotational velocity to the second rotational velocity.

In still a further embodiment, the at least one drive subassembly comprises one of: (i) a plurality of pulleys or a plurality of sprockets operatively coupled to one another by means of a tangential coupling element, or (ii) a plurality of gears.

In yet a further embodiment, the tangential coupling element is selected from the group consisting of a belt and a chain.

In still a further embodiment, the at least one drive subassembly comprises a plurality of drive subassemblies, a first of the plurality of drive subassemblies comprising a first plurality of pulleys or a first plurality of sprockets operatively coupled to one another by means of a first tangential coupling element, and a second of the plurality of drive subassemblies comprising a second plurality of pulleys or a second plurality of sprockets operatively coupled to one another by means of a second tangential coupling element.

In yet a further embodiment, the resistance assembly comprises a flywheel rotationally coupled to the drivetrain assembly and a braking subassembly configured to inhibit a rotational movement of the flywheel.

In still a further embodiment, the braking subassembly of the resistance assembly comprises a plurality of magnets, the plurality of magnets configured to generate an eddy current so as to inhibit the rotational movement of the flywheel.

In yet a further embodiment, the base assembly comprises at least one locking device for attaching the elliptical exercise device to a patient table of the medical imaging device.

In still a further embodiment, the at least one locking device of the base assembly comprises a knob member having a plurality of internal threads and a fastener member having a plurality of external threads, the plurality of external threads on the fastener member configured to engage the plurality of internal threads on the knob member, and the fastener member configured to secure the elliptical exercise device to the patient table of the medical imaging device when the knob member is tightened by a user.

In yet a further embodiment, the medical imaging device to which the elliptical exercise device is configured to be secured comprises one of the following: (i) a magnetic resonance imaging (MRI) device, (ii) a coherence tomography (CT) scanning device, and (iii) an ultrasonic imaging device.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
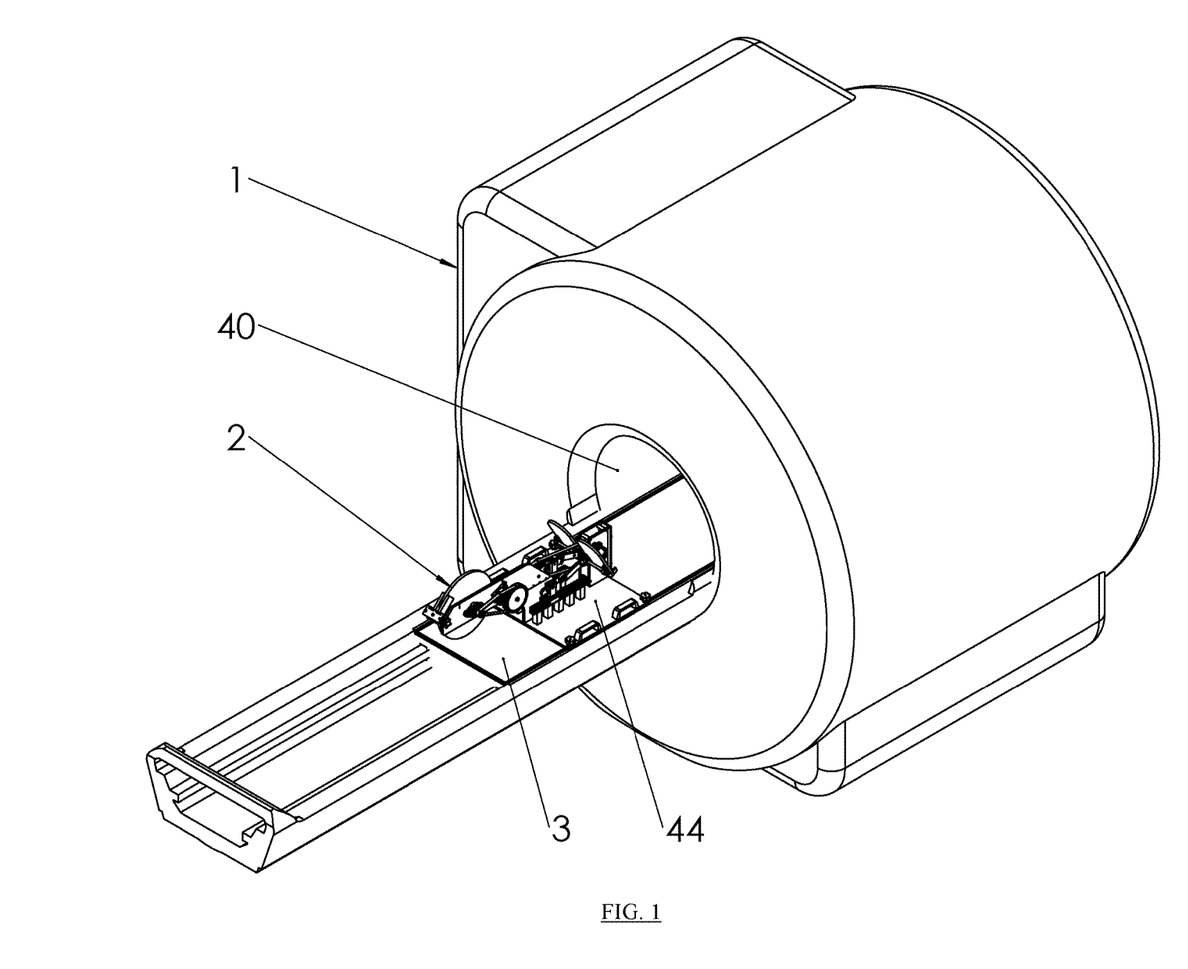
FIG. 1 is a perspective view of a magnetic resonance imaging (MRI) scanner with the elliptical exercise device mounted on the patient table thereof, according to an embodiment of the invention.
Figure 2:
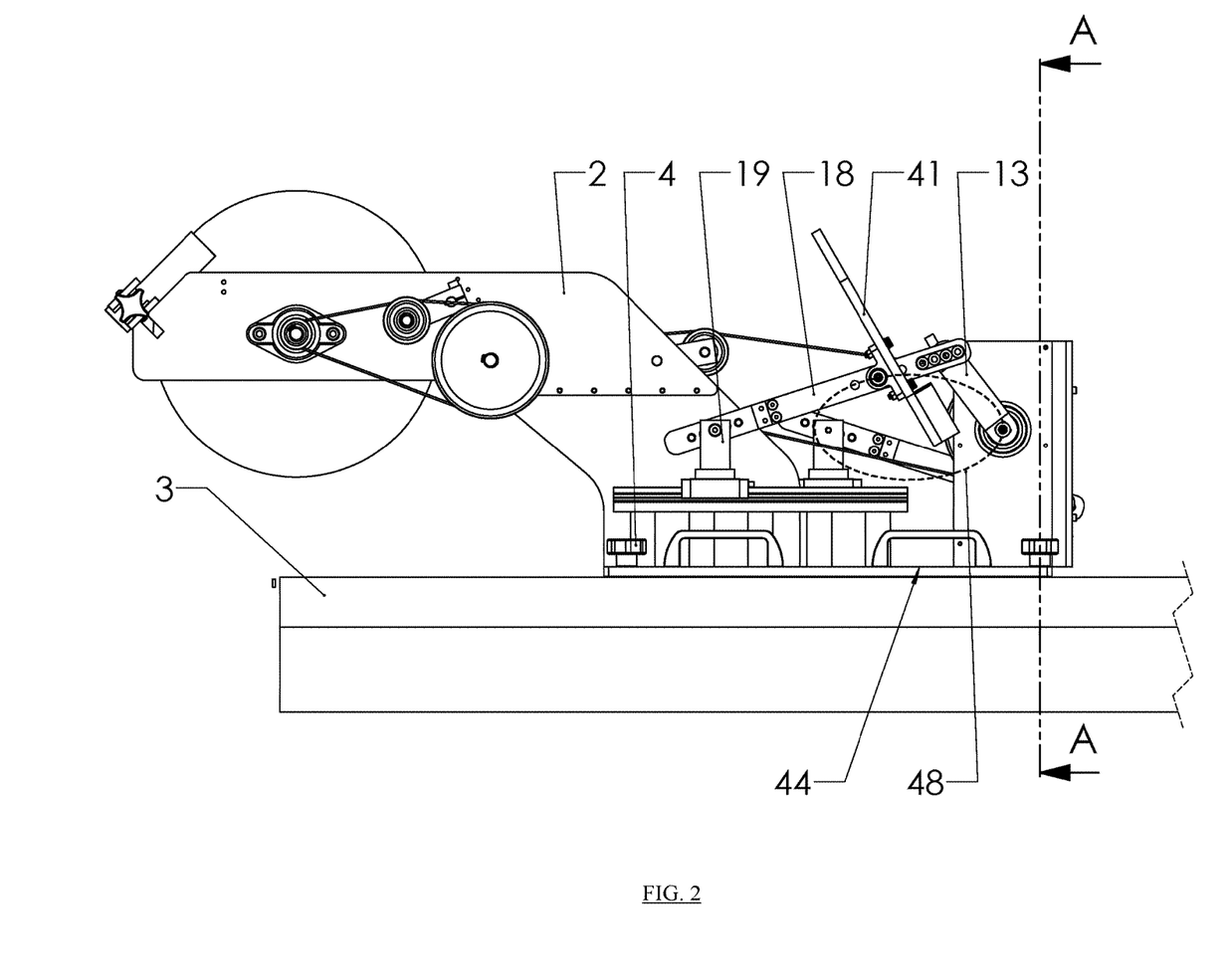
FIG. 2 is a side elevational view of the elliptical exercise device of FIG. 1 mounted on the patient table of the MRI scanner.
Figure 3:
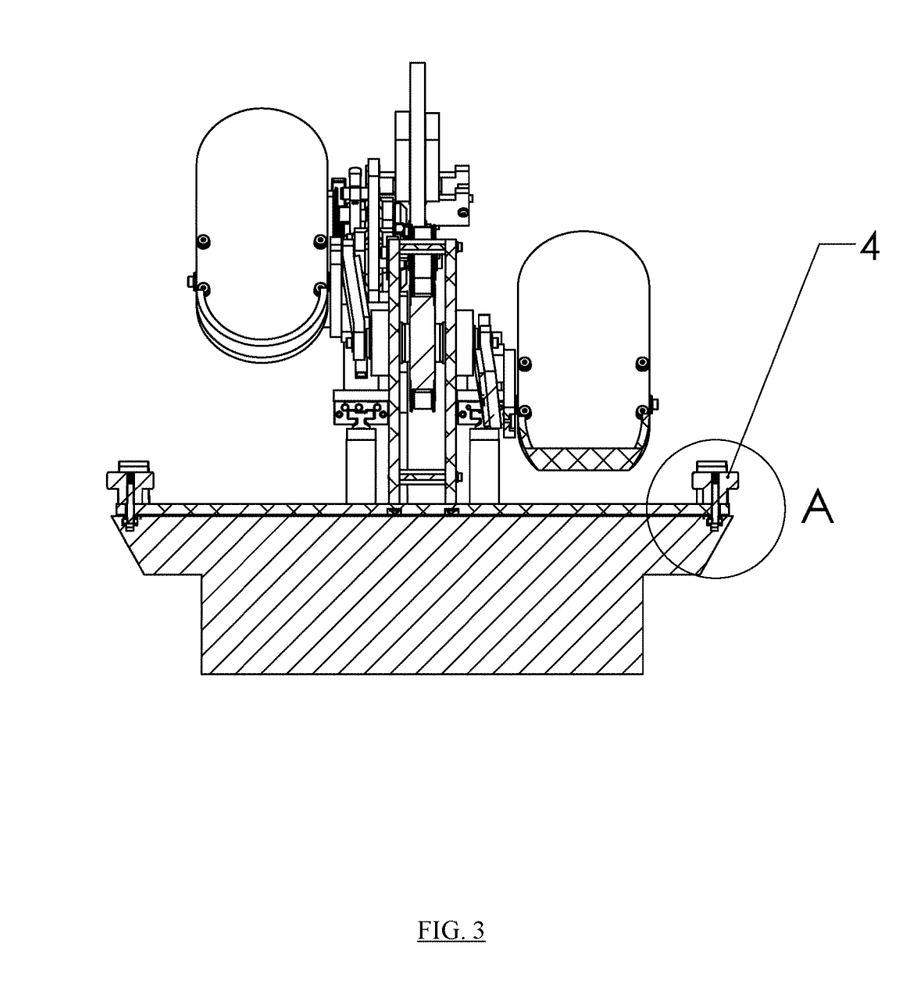
FIG. 3 is a transverse sectional view of the elliptical exercise device of FIG. 1, wherein the section is cut along the cutting plane line A-A in FIG. 2.

In the illustrated embodiment, the elliptical exercise device described herein is compatible with a magnetic resonance imaging (MRI) scanner. That is, the elliptical exercise device is capable of being used in conjunction with the MRI scanner without interfering with the magnetic resonance imaging performed by the MRI scanner. As shown in FIGS. 1 and 2, in the illustrative embodiment, the elliptical exercise device 2 mounts to the patient table 3 of the MRI scanner 1, and may be placed anywhere along the patient table 3 to accommodate patients of varying sizes. As such, the elliptical exercise device 2 moves with the patient table 3 of the MRI scanner 1 when the patient table 3 is displaced (e.g., when the patient is moved into the interior of the MRI bore 40). In general, the patient interface of the elliptical exercise device 2 comprises two pedals that provide resistance when rotated. As will be described in detail hereinafter, in the illustrative embodiment, an eddy current braking system is used to provide this resistance by utilizing a flywheel 9 (see FIGS. 5, 6, and 10) that is attached to a two stage drive system, which allows the flywheel 9 to rotate nine (9) times for each revolution of the pedal crank arm 13.

In an exemplary embodiment, the MRI scanner 1 may comprise a 3 Tesla MRI scanner, such as the Siemens® Magnetom Skyra scanner, or another MRI scanner made by Philips®, GE®, or Toshiba®. The magnetic field generated by the MRI scanner 1 is the strongest at the center of the MRI bore 40, and then decreases as the distance from the center of the MRI bore 40 increases (e.g., the magnetic field strength is generally proportionate to the inverse square of the distance from the center of the MRI bore 40). As such, a higher magnetic field exists close to the MRI bore 40, as compared to a distance three (3) feet away from the MRI bore 40. In other embodiments, rather than being used with an MRI scanner 1, the elliptical exercise device 2 described herein may be used with other types of medical imaging devices, such as coherence tomography (CT) scanning devices and ultrasonic imaging devices.

Figure 6:
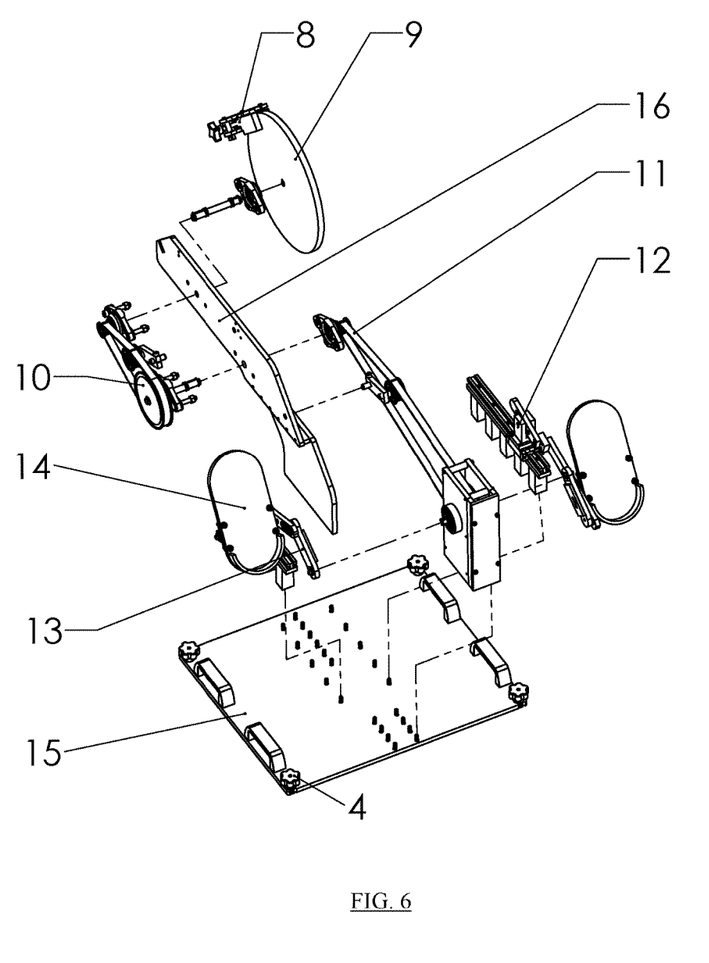
FIG. 6 is an exploded top perspective view of the elliptical exercise device of FIG. 1.
Figure 7:
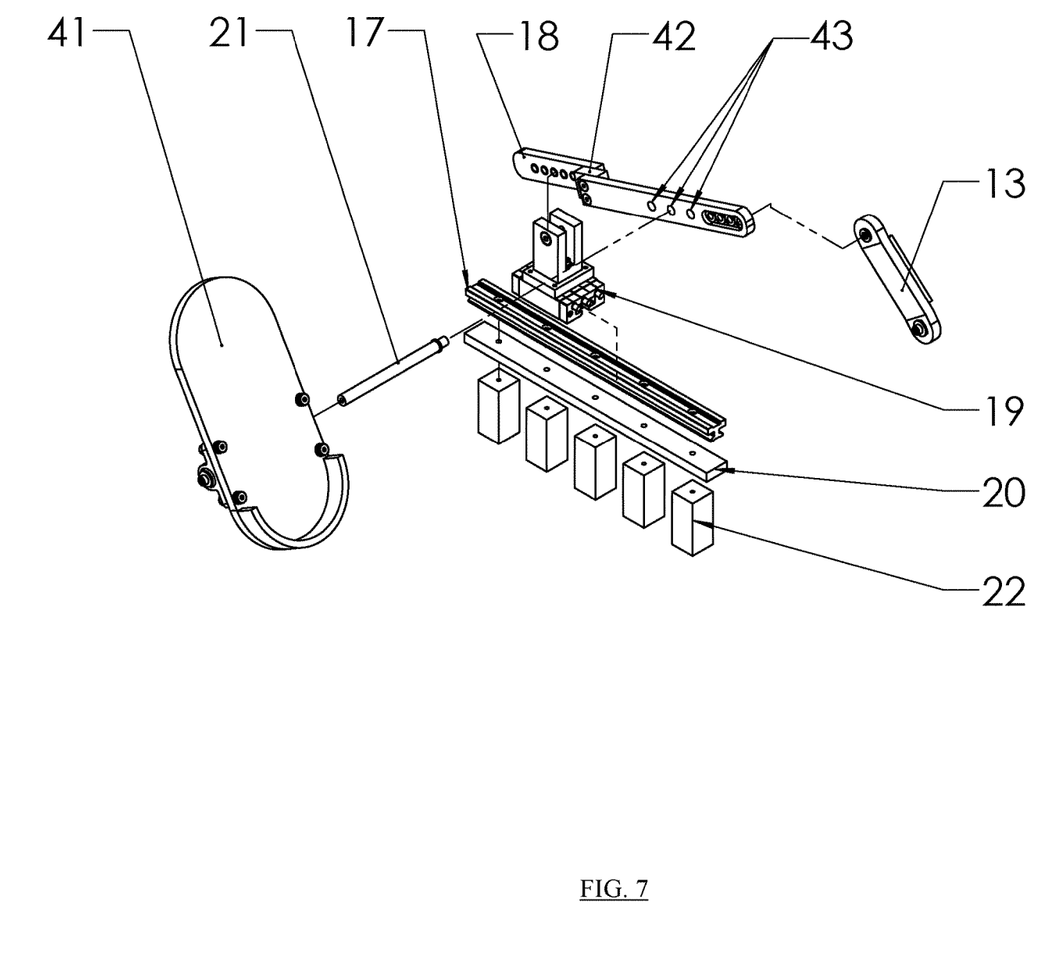
FIG. 7 is an exploded view of the left one of the pedal and linear sliding assemblies of the elliptical exercise device of FIG. 1.

For cardiac imaging, the patient's heart needs to be at iso-center, which is in the center of the MRI bore 40 (see FIG. 1) which, when simplified, is generally in the shape of a half cylinder. When the patient is positioned at iso-center, his or her legs extend out of the bore 40 of the MRI scanner 1 at varying distances based on patient biomechanics. To address patient knee clearance issues with the top of the MRI bore 40, the illustrated embodiment of the elliptical exercise device 2 utilizes a slider linkage to allow the pedals to follow an elliptical shape that flattens (or lowers) the pedal height and subsequent patient knee height. Each pedal is connected to a linkage that attaches to a slider on one side and a crank arm (linkage) on the other. The crank arm attaches to a spindle that attaches to another crank arm on the opposing side. In the illustrative embodiment, bearings are used to reduce friction as the crank arms are rotated. Having the pedals 41 attach to a link 18 that is connected (at a certain distance) on one side to a crank arm 13 that follows a circular path and a slider 19 on the other side allows the pedal 41 to follow an elliptical path 48 (see FIG. 2). As illustrated in FIGS. 6 and 7 below, the elliptical path is controlled by the following parameters: (i) position of pedal relative to the connection of the crank, (ii) length of crank, (iii) position of center of rotation of crank, (iv) position of pedal relative to the slider mechanism, and (v) position of slider mechanism.

Now, with initial reference to FIG. 5, an illustrative embodiment of the elliptical exercise device 2 will be described. With reference to this figure, it can be seen that the elliptical exercise device 2 generally comprises a pedal assembly 14, the pedal assembly 14 includes a pair of pedal members 41 configured to receive respective forces exerted thereon by a user disposed in a generally supine position, the pedal members 41 are configured to rotate in an elliptical pedal path when the forces are exerted thereon; a drivetrain assembly 10, 11 operatively coupled to the pedal assembly 14; and a resistance assembly 8, 9 operatively coupled to the drivetrain assembly 10, 11, the drivetrain assembly 10, 11 configured to transfer the motive power generated by the user from the pedal assembly 14 to the resistance assembly 8, 9, and the resistance assembly 8, 9 configured to provide a resistance force to oppose a rotational movement of one or more components 9 of the resistance assembly 8, 9. In the illustrated embodiment, the elliptical exercise device 2 may be in the form of an ergometer with means for measuring the work performed by the user when exercising (i.e., power and cadence may be measured). For example, a wireless transducer comprising a plurality of strain gages may be mounted to the crank arm 13 in order to determine the deflection of the crank arm 13, which enables the power exerted on the crank arm 13 to be determined. Also, the elliptical exercise device 2 may include an accelerometer for measuring the cadence value of the user.

Figure 5:
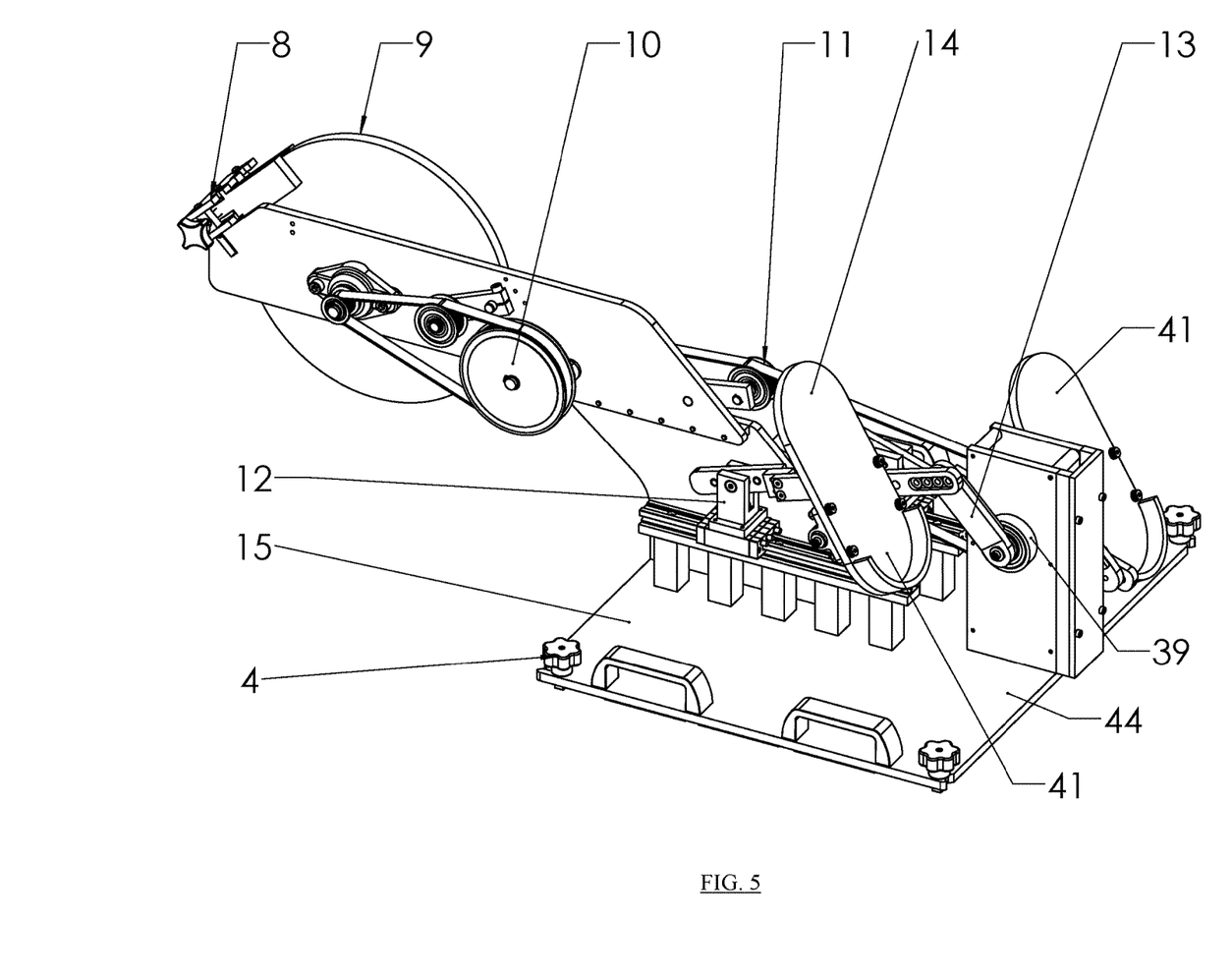
FIG. 5 is a perspective view of the elliptical exercise device of FIG. 1 shown removed from the magnetic resonance imaging (MRI) scanner.

As shown in the illustrative embodiment of FIG. 5, it can be seen that the elliptical exercise device 2 further comprises a linear sliding assembly 12 operatively coupled to the pedal assembly 14. In particular, with combined reference to FIGS. 5-7, it can be seen that the linear sliding assembly 12 includes a slider linkage member 18, a slider carriage member 19, a slide rail 17, and a crank arm 13 for each of the right and left pedal members 41. Each slider linkage member 18 operatively couples a respective pedal member 41 to a respective bracket portion of the slider carriage member 19. Each slider carriage member 19 slidingly engages its respective slide rail 17 so as to create the elliptical pedal path. Each crank arm 13 transmits the motive power generated from the pedaling by the user to the drivetrain assembly 10, 11. Referring to the exploded view of FIG. 7, it can be seen that a slide rail support member 20 is provided underneath the slide rail 17. The slide rail support member 20 is supported on a plurality of spaced-apart slider spacer members 22, which are attached to the base plate member 15. During pedaling, each slider carriage member 19 slides bank-and-forth on its respective slide rail 17. Pads disposed on the bottom of the carriage member 19 facilitate its linear translation back-and-forth along its respective slide rail 17.

Also, as depicted in FIG. 7, it can be seen that each slider linkage member 18 comprises a plurality of apertures 43 spaced apart along a length thereof for enabling the elliptical pedal path to be varied (e.g., by inserting the pedal connector rod or spindle 21 through a selected one of the apertures 43). For example, in the illustrated embodiment, the pedal connector rod 21 is inserted through the center one of the plurality of spaced-apart apertures 43. Also, each slider linkage member 18 further comprises an offset portion 42 for providing the requisite clearance in the assembly 12. Referring again to FIG. 7, it can be seen that each pedal member 41 of the pedal assembly 14 is connected to its respective slider linkage member 18 by means of the respective pedal connector rod 21. In an exemplary embodiment, the crank arm 13 and the pedal connector rod 21 may each be formed from a brass material so as to prevent the induction of eddy currents near the MRI bore 40 (i.e., because brass has a low electrical conductivity).

Next, with reference to FIGS. 5, 6, 11, and 12, the drivetrain assembly 10, 11 of the elliptical exercise device 2 will be explained in detail. In the illustrative embodiment, the crank arms 13 of the linear slide assembly 12 are configured to rotate at a first rotational velocity and the flywheel 9 of the resistance assembly 8, 9 is configured to rotate at a second rotational velocity that is greater than the first rotational velocity of the crank arms 13. Also, in the illustrative embodiment, the drivetrain assembly 10, 11 comprises a plurality of drive subassemblies (i.e., a first stage drive system 11 and a second stage drive system 10). The plurality of drive subassemblies 10, 11 are configured to produce the increase from the first rotational velocity to the second rotational velocity. As best shown in the exploded view of FIG. 6, the plurality of drive subassemblies 10, 11 are supported on the drive frame member 16. In the illustrative embodiment, as shown in FIG. 12, a first of the plurality of drive subassemblies (i.e., the first stage drive system 11) comprises a first plurality of pulleys 30, 33 operatively coupled to one another by means of a first tangential coupling element 35. More specifically, in the illustrated embodiment, a first large pulley 33 may be coupled to a second small pulley 30 by means of the belt 35. For example, the first large pulley 33 may comprise a 72-tooth pulley, while the second small pulley 30 may comprise a 16-tooth pulley. In the illustrated embodiment, the large pulley 33 is affixed to, and rotates with a crank arm spindle 38, which is attached to each of the crank arms 13. Also, as shown in FIGS. 5 and 12, the crank arm spindle 38 is rotatably supported on a pair of ball bearing assemblies 39 that include ball bearings 37 (e.g., glass ball bearings), each of which is disposed within a ball bearing housing 36. The ball bearing assemblies 39 and the crank arm spindle 38 are supported on base plate member 15 by means of the spindle support frame assembly 34. In addition, in FIG. 12, it can be seen that the first stage drive system 11 further comprises a belt tensioner assembly 32 for maintaining the proper tension on the belt 35. For example, the belt tensioner assembly 32 may comprise ball-bearings formed from 304 stainless steel. Similar to that described above for the crank arms 13 and the pedal connector rods 21, the crank arm spindle 38 may also be formed from a non-electrically conductive brass material so as to prevent the induction of eddy currents (i.e., because the crank arm spindle 38 is also close to the MRI bore 40).

Figure 11:
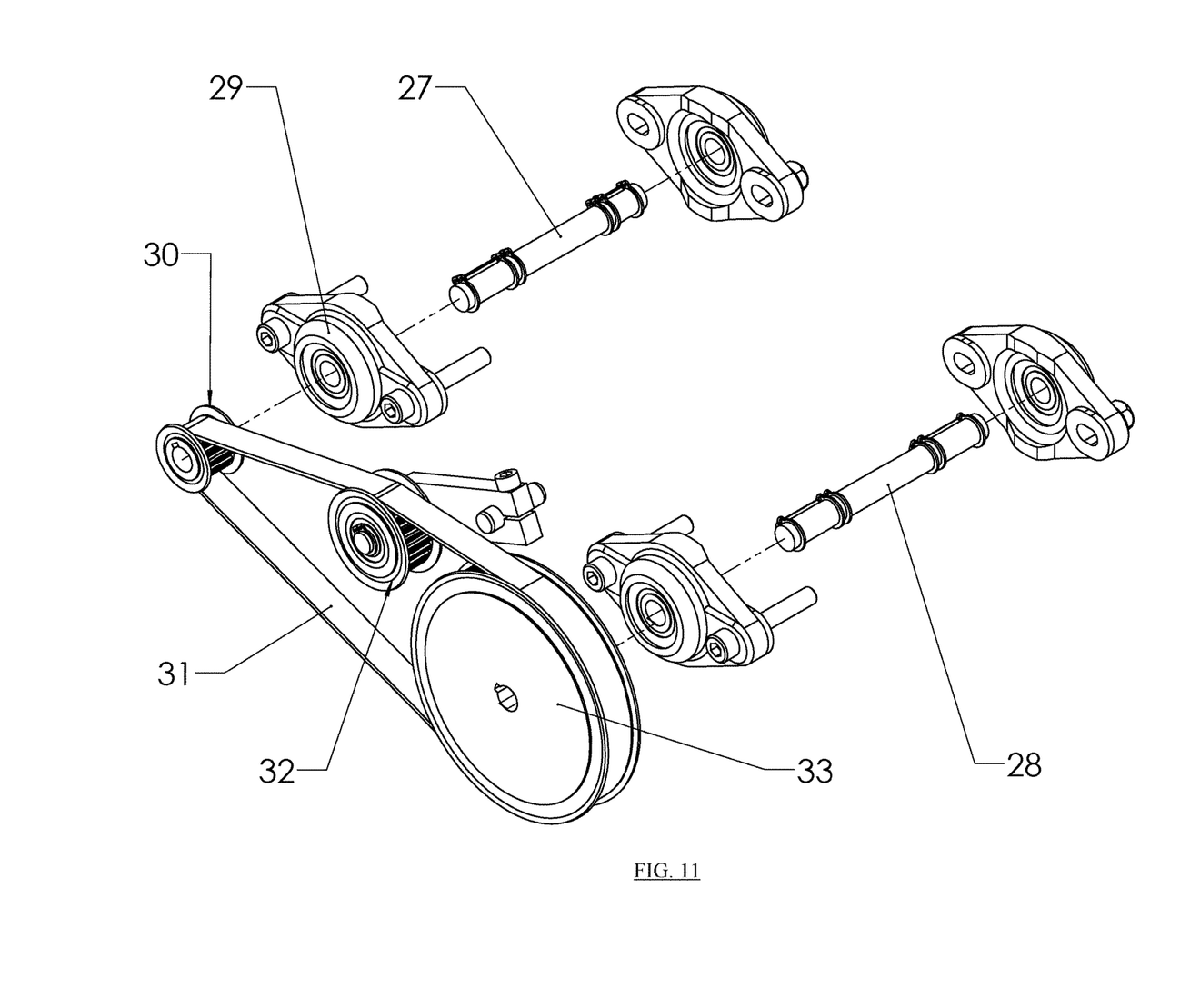
FIG. 11 is an exploded perspective view of a second one of the drive subassemblies of the drivetrain assembly of the elliptical exercise device of FIG. 1.
Figure 12:
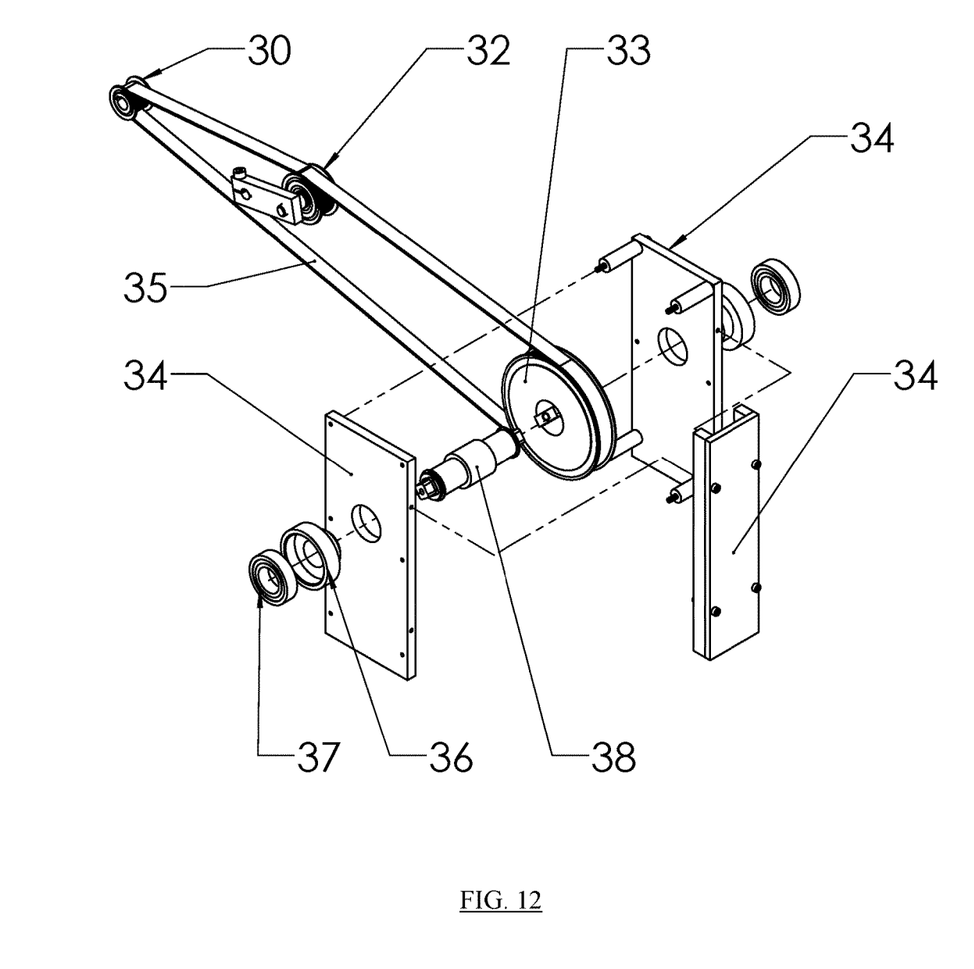
FIG. 12 is an exploded perspective view of a first one of the drive subassemblies of the drivetrain assembly of the elliptical exercise device of FIG. 1.

Turning to FIG. 11, a second of the plurality of drive subassemblies (i.e., the second stage drive system 10) of the illustrative embodiment will be described. Similar to that described above for the first stage drive system 11, the second stage drive system 10 comprises a second plurality of pulleys 30, 33 operatively coupled to one another by means of a second tangential coupling element 31. More specifically, in the illustrated embodiment, a first large pulley 33 may be coupled to a second small pulley 30 by means of the belt 31. For example, as in the first stage drive system 11, the first large pulley 33 may comprise a 72-tooth pulley, while the second small pulley 30 may comprise a 16-tooth pulley. In the illustrated embodiment, the large pulley 33 rotates together with the first stage to second stage axle assembly 28, which connects the first and second stages to one another, while the small pulley 30 rotates together with the flywheel axle assembly 27, which connects the small pulley 30 to the flywheel 9. Also, as shown in FIG. 11, the flywheel axle assembly 27 and the first stage to second stage axle assembly 28 are each rotatably supported on a pair of pillow block bearings 29 (e.g., bearings supported in a plastic housing). In addition, in FIG. 11, it can be seen that the second stage drive system 10, like the first stage drive system 11 described above, also includes a belt tensioner assembly 32 for maintaining the proper tension on the belt 31.

In the illustrative embodiment, the flywheel 9 is rotated through the two stage drive system 10, 11 that connects the pedal crank assembly 13, 38 to the flywheel 9. In an exemplary embodiment, each stage is geared at 4.5:1 yielding a 9:1 ratio at the flywheel 9. As such, each single revolution of the crank assembly 13, 38 produces nine (9) revolutions of the flywheel 9. Advantageously, the two stage drive system 10, 11 allows the drivetrain assembly 10, 11 of the elliptical exercise device 2 to meet the space constraints associated with the mounting of the elliptical exercise device 2 on the MRI scanner 1. While pulleys 30, 33 and belts 31, 35 are utilized in the illustrated embodiment of the two stage drive system 10, 11 described herein, it is to be understood that the two stage drive system 10, 11 could alternatively utilize sprockets with tangential coupling elements in the form of chains for transferring the motive power to the flywheel 9.

Figure 8:
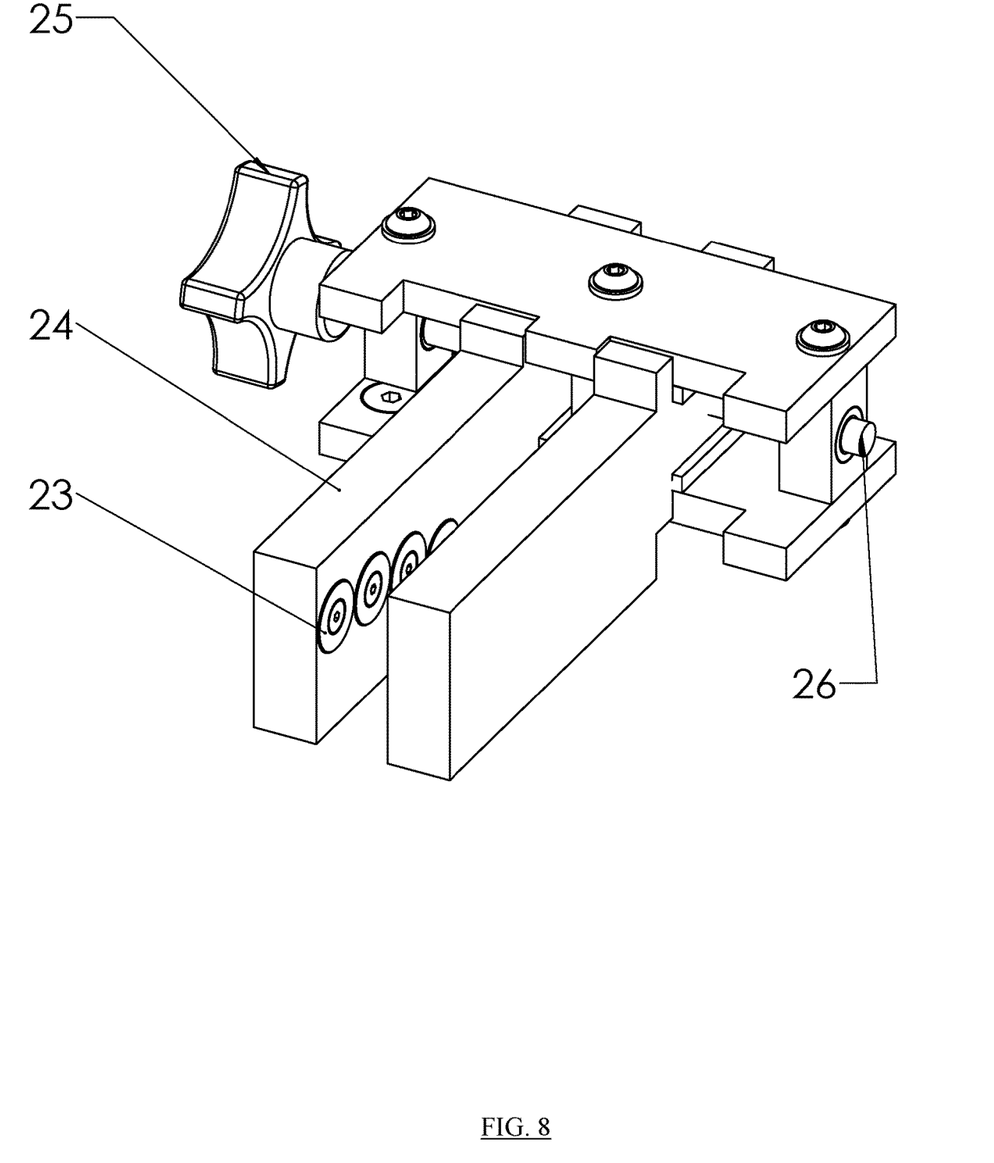
FIG. 8 is a perspective view of the braking subassembly of the resistance assembly of the elliptical exercise device of FIG. 1.
Figure 9:
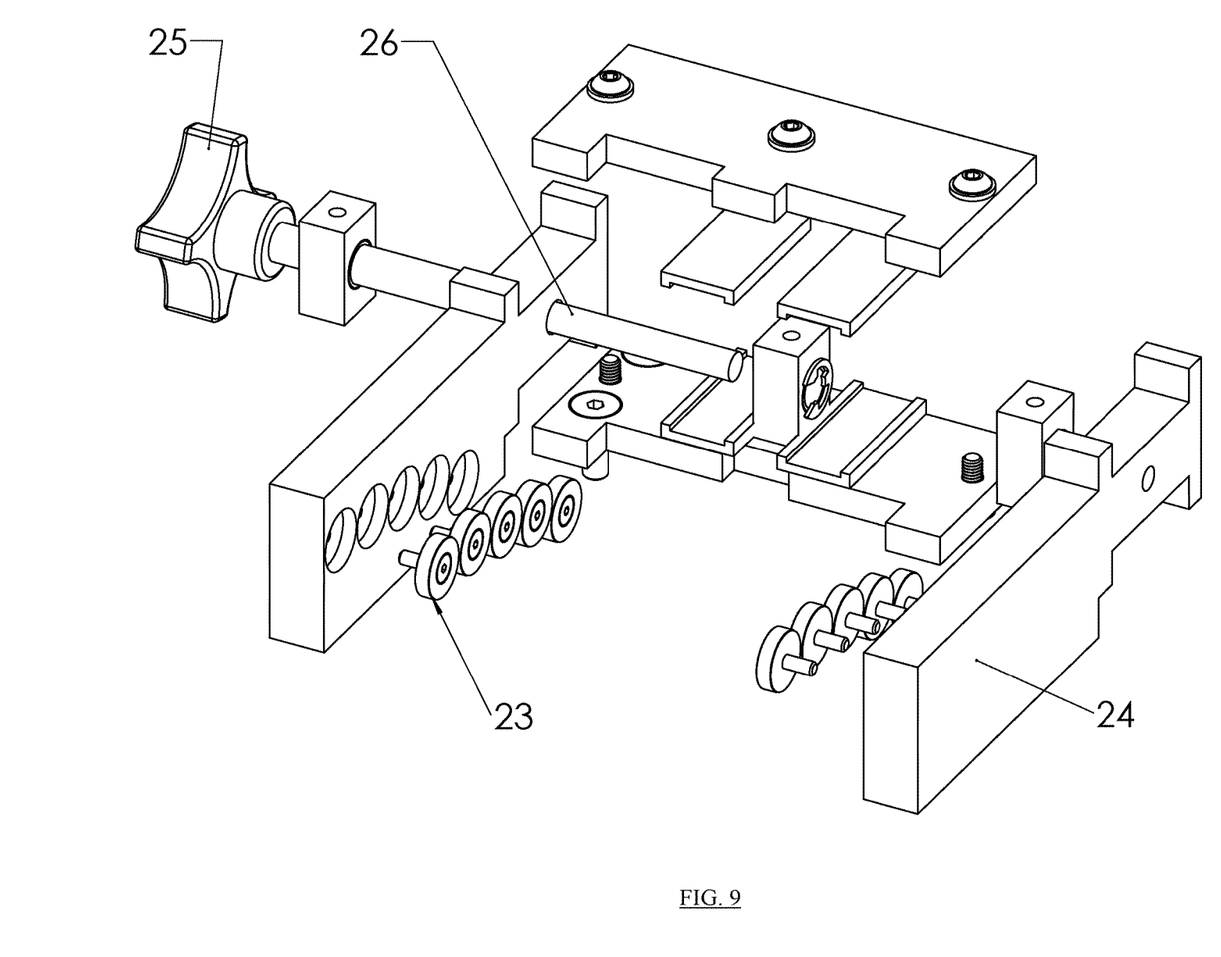
FIG. 9 is an exploded perspective view of the braking subassembly of FIG. 8.
Figure 10:
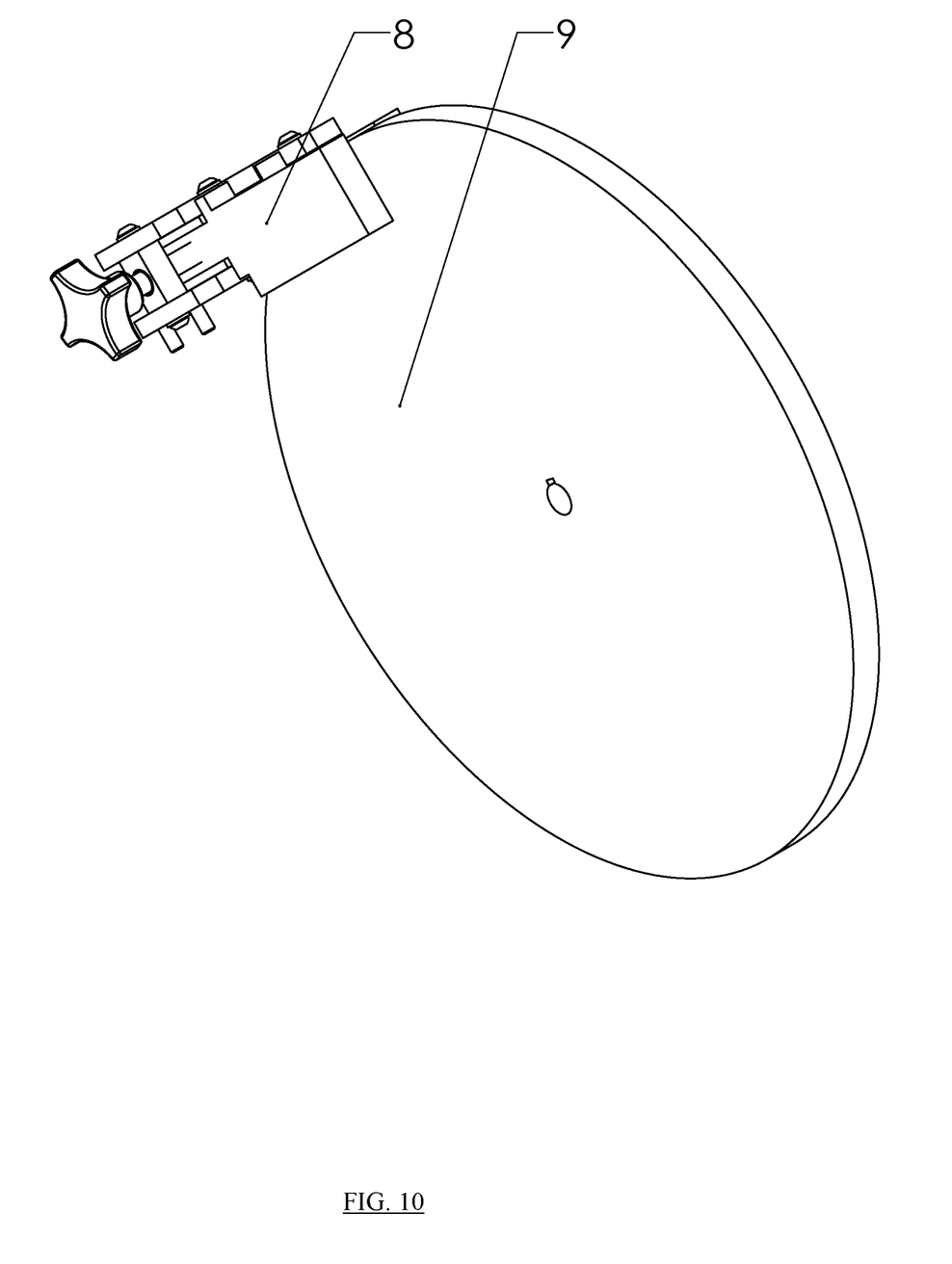
FIG. 10 is a perspective view of the resistance assembly of the elliptical exercise device of FIG. 1.

Now, referring to FIGS. 8-10, the resistance assembly 8, 9 of the elliptical exercise device 2 will be described in detail. Initially, as shown in FIG. 10, it can be seen that the resistance assembly 8, 9 generally comprises a flywheel 9 and a braking subassembly 8 configured to inhibit a rotational movement of the flywheel 9. The flywheel 9 is rotationally coupled to the drivetrain assembly 10, 11 in the manner described above. Turning to FIGS. 8 and 9, it can be seen that the braking subassembly 8 of the resistance assembly 8, 9 includes a plurality of spaced-apart magnets 23 disposed on each of the opposite sides of the flywheel 9. The plurality of magnets 23 generate an eddy current in order to inhibit the rotational movement of the flywheel 9, and provide providing pedaling resistance to the user of the elliptical exercise device 2. More particularly, as shown in FIGS. 8 and 9, each plurality of magnets 23 is disposed within a respective brake arm 24. The spacing between the brake arms 24 is adjustably controlled by means of the knob 25 and a threaded shaft 26 that is attached to the knob 25 and the brake arms 24. A user may increase or decrease the spacing between the brake arms 24 and the flywheel 9 by rotating the knob 25 in the corresponding rotational direction (i.e., in either a clockwise or counter-clockwise rotational direction). The spacing between the brake arms 24 and the flywheel 9, in turn, controls the amount of resistance opposing the rotational movement of the flywheel 9. As such, the knob 25 allows the user to control the amount of resistance of the elliptical exercise device 2 in order to make the pedaling less challenging or more challenging for the user (e.g., the resistance could be increased in order to elevate the heart rate of the patient). In an exemplary embodiment, the magnets 23 are in the form of neodymium magnets (NdFeB magnets), but other suitable magnets may also be used. The magnitude of the resistance to the rotational movement of the flywheel 9 may also be varied by selecting various types of magnets.

In the illustrative embodiment, eddy current braking is utilized to provide the resistance to the pedaling of the user, but it is to be understood that other forms of resistance (e.g., friction, fluid, etc.) may also be used. In the eddy braking system of the illustrative embodiment, the following are main factors that control resistance: (i) magnet strength, (ii) electrical conductivity of moving material (i.e., the flywheel material), (iii) speed of moving material, and (iv) the distance of magnets with respect to moving material (i.e., the flywheel material). Advantageously, the eddy current braking utilized in the illustrative embodiment described herein involves no physical contact between parts to generate resistance, thus eliminating component wear and preventing the introduction of debris in the hospital room where the medical imaging device is located. As such, the cleanliness of the hospital room is not compromised by the use of the elliptical exercise device 2 in the hospital room with the medical imaging device. Instead of using friction as a form of resistance, the movement of a highly electrically conductive material in a magnetic field (using rare earth magnets) will generate eddy currents due to the changing magnetic field. These eddy currents produce their own magnetic fields which oppose the magnetic field produced by the rare earth magnets so as to cause resistance. In an exemplary embodiment, the flywheel 9 is formed from 6061 aluminum (i.e., a moving electrically conductive material), but other suitable electrically conductive materials may also be used for the flywheel 9. The series of rare earth magnets 23, which are positioned on the opposing brake arms 24, extend over the flywheel (see FIG. 10). The knob 25 controls the position of each brake arm 24 with respect to the face of the rotating flywheel 9 so as to control the distance between each brake arm 24 and the flywheel 9, thereby regulating the resistance to the rotational movement of the flywheel 9.

In the illustrative embodiment, because the magnets 23 are placed into a magnetic field generated by the MRI scanner 1, small magnets (e.g., 0.5 in. diameter) are used to minimize forces generated for safety purposes. Because of the small magnets used, the speed of the flywheel 9 is required to compensate for this to generate ample resistance in the brake system. In the illustrative embodiment, the magnetic field outside of the bore of the 3 T (Tesla) MRI scanner yields a much lower magnetic field thirty-six (36) inches from the MRI bore 40, which allows the magnets 23 to be used in this area but requires the device 2 to be extended (see FIG. 5, the magnets 23 are thirty-six (36) inches away from the MRI bore 40 so that they do not interfere with the operation of the MRI scanner 1).

Figure 4:
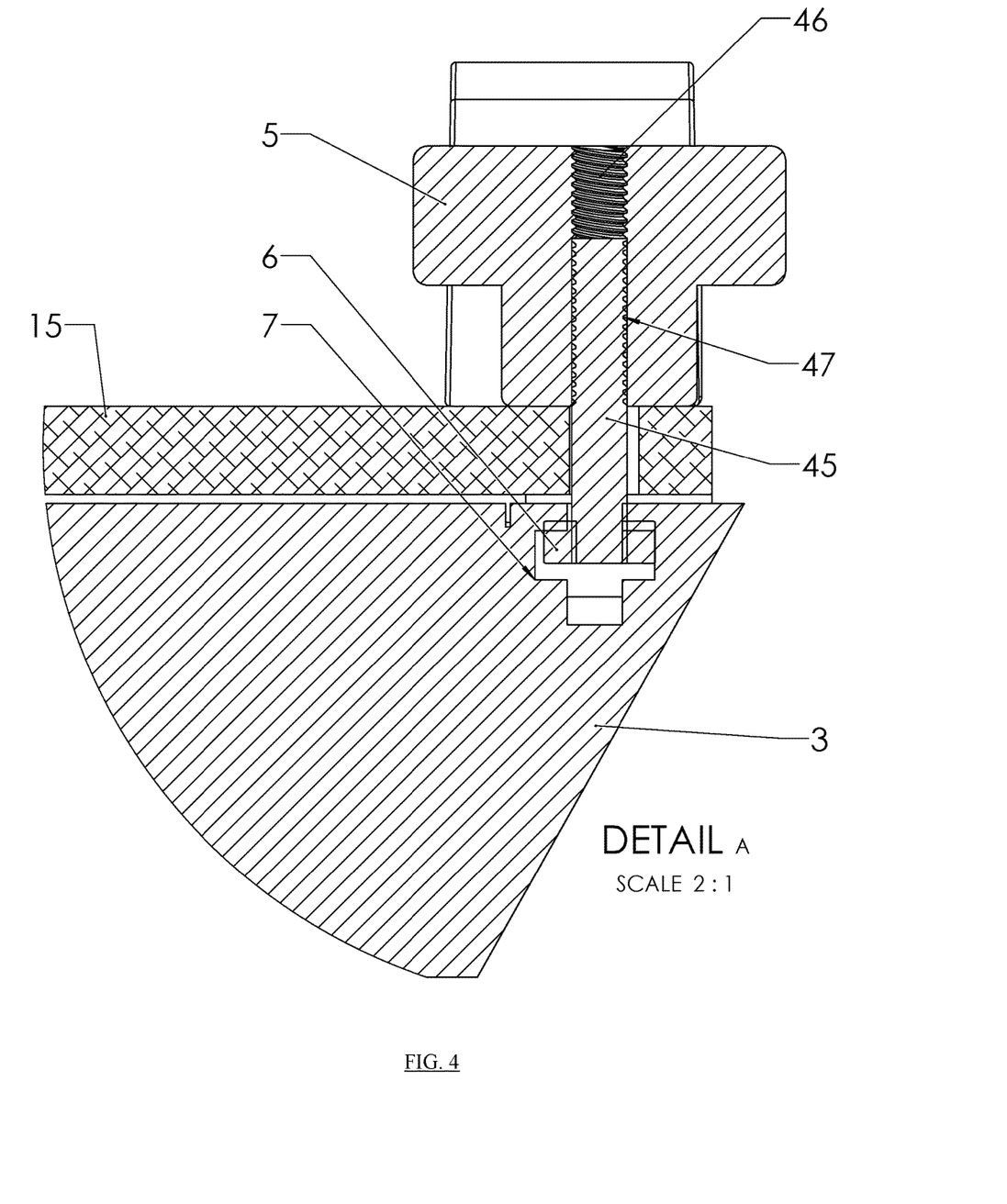
FIG. 4 is a partial enlarged view of the locking device of the base assembly of the elliptical exercise device of FIG. 3 (Detail "A")

Finally, referring again to FIGS. 1-5, the base assembly 44 of the elliptical exercise device 2 of the illustrative embodiment will be explained. As shown in FIG. 5, the linear sliding assembly 12 and the pedal assembly 14 are mounted on the base assembly 44. Referring to FIGS. 1-4, it can be seen that the base assembly 44 is attached to the medical imaging device (i.e., MRI scanner 1) so as to secure the elliptical exercise device 2 to the patient table 3 of the MRI scanner 1. With reference again to FIG. 5, the base assembly 44 includes a base plate member 15 and a plurality of locking devices 4 for attaching the elliptical exercise device 2 to the patient table 3 of the MRI scanner 1. For example, in the illustrated embodiment, a locking device 4 is provided in each of the four (4) corners of the base plate member 15 (e.g., see FIG. 5). Turning to the detail view of FIG. 4, each locking device 4 of the base assembly 44 generally comprises a knob member 5 having a plurality of internal threads 46 and a fastener member 45 having a plurality of external threads 47. The plurality of external threads 47 on the fastener member 45 engage the plurality of internal threads 46 on the knob member 5 such that the fastener member 45 secures the elliptical exercise device 2 to the patient table 3 of the MRI scanner 1 when the knob member 5 is tightened by a user. As shown in FIG. 4, in the illustrated embodiment, the fastener member 45 of the locking device 4 is provided with a T-nut 6 for engaging with a channel or slot 7 in the patient table 3 of the MRI scanner 1. In this manner, each locking device 4 secures the base plate member 15 of the elliptical exercise device 2 to the patient table 3 of the MRI scanner 1.

In alternative embodiments, when the elliptical exercise device 2 is secured to other MRI scanners that have channels or slots with cross-sectional shapes that are different from the channel or slot 7 of the illustrative embodiment, different-shaped nuts may be used for securing the elliptical exercise device 2 to the patient table. For example, when the elliptical exercise device 2 is secured to the patient table of an MRI scanner having slots with a trapezoidal cross-sectional shape, the nuts may have a corresponding trapezoidal cross-section shape. As another example, when the elliptical exercise device 2 is secured to the patient table of an MRI scanner having slots with a circular cross-sectional shape, the nuts may have a corresponding circular cross-section shape.

It is readily apparent that the aforedescribed elliptical exercise device 2 offers numerous advantages. First, the elliptical exercise device 2 is capable of being used by a person (e.g., a patient) disposed in a supine position. Secondly, the elliptical exercise device 2 is compatible with medical imaging devices, such as MRI scanner 1, so that a patient may use the exercise device 2 just prior to the image of the patient's body being captured by the imaging device. The elliptical exercise device 2 described herein is designed as a non-ferrous device so that it does not interfere with the imaging performed by the medical imaging device. As such, the elliptical exercise device 2 may be used in any study that requires an investigation of increased cardiac stress on the patient. Finally, the elliptical exercise device 2 minimizes the patient knee height during exercising so that the exercise device 2 is compatible with the knee clearance requirements of the medical imaging device. For example, the elliptical exercise device 2 is compatible with the knee clearance requirements of an MRI scanner 1 (e.g., the knees of the patient do not conflict with the top of the MRI bore 40 when the patient is exercising while lying on the patient table 3 of the MRI scanner 1.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An elliptical exercise device configured to be utilized with a medical imaging device, said elliptical exercise device comprising:
  a pedal assembly, said pedal assembly including at least one pedal member configured to receive a force exerted thereon by said user, said at least one pedal member configured to rotate in an elliptical pedal path when said force is exerted thereon;
  a linear sliding assembly operatively coupled to said pedal assembly, said linear sliding assembly including a slider carriage member, a slide rail, and one or more spacer members disposed underneath said slide rail, said slider carriage member configured to slidingly engage said slide rail so as to create said elliptical pedal path;
  a drivetrain assembly operatively coupled to said pedal assembly;
  a resistance assembly operatively coupled to said drivetrain assembly, said drivetrain assembly configured to transfer the motive power generated by said user from said pedal assembly to said resistance assembly, and said resistance assembly configured to provide a resistance force to oppose a rotational movement of one or more components of said resistance assembly;

a drive frame member supporting said drivetrain assembly and said resistance assembly; and a base assembly coupled to said pedal assembly, said base assembly defining a footprint, said base assembly having a first end and a second end disposed opposite to said first end, said first end configured to be disposed closer to a torso of said user than said second end, said pedal assembly being disposed closer to said first end of said base assembly than said second end, said drive frame member extending beyond said second end of said base assembly so as to support said resistance assembly outside said footprint of said base assembly, and said slide rail being attached to and spaced apart from a top surface of said base assembly by said one or more spacer members, said base assembly configured to be attached to said medical imaging device so as to secure said elliptical exercise device to a portion of said medical imaging device.

2. The elliptical exercise device according to claim 1, wherein said linear sliding assembly further comprises a slider linkage member and a crank arm, said slider linkage member operatively coupling said pedal assembly to said slider carriage member, and said crank arm configured to transmit said motive power to said drivetrain assembly; and wherein said one or more spacer members disposed underneath said slide rail comprise a plurality of spacer members spaced apart from one another along a length of said slide rail.

3. The elliptical exercise device according to claim 2, wherein said crank arm of said linear sliding assembly is configured to rotate at a first rotational velocity and said one or more components of said resistance assembly is or are configured to rotate at a second rotational velocity, said second rotational velocity being greater than said first rotational velocity; and wherein said drivetrain assembly comprises at least one drive subassembly, said at least one drive subassembly configured to produce the increase from said first rotational velocity to said second rotational velocity.

4. The elliptical exercise device according to claim 3, wherein said at least one drive subassembly comprises one of: (i) a plurality of pulleys or a plurality of sprockets operatively coupled to one another by means of a tangential coupling element, or (ii) a plurality of gears.

5. The elliptical exercise device according to claim 4, wherein said tangential coupling element is selected from the group consisting of a belt and a chain.

6. The elliptical exercise device according to claim 3, wherein said at least one drive subassembly comprises a plurality of drive subassemblies, a first of said plurality of drive subassemblies comprising a first plurality of pulleys or a first plurality of sprockets operatively coupled to one another by means of a first tangential coupling element, and a second of said plurality of drive subassemblies comprising a second plurality of pulleys or a second plurality of sprockets operatively coupled to one another by means of a second tangential coupling element.

7. The elliptical exercise device according to claim 1, wherein said resistance assembly comprises a flywheel rotationally coupled to said drivetrain assembly and a braking subassembly configured to inhibit a rotational movement of said flywheel.

8. The elliptical exercise device according to claim 7, wherein said braking subassembly of said resistance assembly comprises a plurality of magnets, said plurality of magnets configured to generate an eddy current so as to inhibit said rotational movement of said flywheel.

9. The elliptical exercise device according to claim 1, wherein said base assembly comprises at least one locking device for attaching said elliptical exercise device to a patient table of said medical imaging device.

10. The elliptical exercise device according to claim 9, wherein said at least one locking device of said base assembly comprises a knob member having a plurality of internal threads and a fastener member having a plurality of external threads, said plurality of external threads on said fastener member configured to engage said plurality of internal threads on said ti knob member, and said fastener member configured to secure said elliptical exercise device to said patient table of said medical imaging device when said knob member is tightened by a user.

11. The elliptical exercise device according to claim 1, wherein said medical imaging device to which said elliptical exercise device is configured to be secured comprises one of the following: (i) a magnetic resonance imaging (MRI) device, (ii) a coherence tomography (CT) scanning device, and (iii) an ultrasonic imaging device.

* * * * *